United States Patent [19]

Yang et al.

[11] Patent Number: 4,882,156
[45] Date of Patent: Nov. 21, 1989

[54] CONFECTIONERY DELIVERY SYSTEM FOR EXPECTORANTS

[75] Inventors: Robert K. Yang, Randolph; Shri C. Sharma, Mendham; Shan-Shan Sheu, Parsippany; James J. Shaw, Morristown, all of N.J.

[73] Assignee: Warner Lambert Co., Morris Plains, N.J.

[21] Appl. No.: 258,248

[22] Filed: Oct. 14, 1988

Related U.S. Application Data

[62] Division of Ser. No. 811,601, Dec. 20, 1985, Pat. No. 4,778,676.

[51] Int. Cl.$^4$ ............................ A61K 9/20; A61K 9/28
[52] U.S. Cl. ................................. 424/440; 424/441; 424/465; 424/484; 424/499; 424/496; 424/498; 424/502; 514/948; 514/960
[58] Field of Search ............................ 424/440, 441

[56] References Cited

U.S. PATENT DOCUMENTS

| | | | |
|---|---|---|---|
| 4,452,821 | 6/1984 | Gergely | 426/5 |
| 4,551,331 | 11/1985 | Rudin | 424/195.1 |
| 4,565,702 | 1/1986 | Morley et al. | 426/93 |
| 4,568,557 | 2/1986 | Becker et al. | 426/618 |
| 4,632,821 | 12/1986 | Peters et al. | 424/15 |
| 4,643,898 | 2/1987 | Peters et al. | 424/155 |
| 4,647,459 | 3/1987 | Peters et al. | 424/155 |
| 4,668,519 | 5/1987 | Dartey et al. | 426/548 |
| 4,673,578 | 6/1987 | Becker et al. | 426/93 |
| 4,678,672 | 7/1987 | Dartey et al. | 426/19 |
| 4,695,463 | 9/1987 | Yang et al. | 424/440 |
| 4,710,390 | 12/1987 | Schumacher | 426/285 |
| 4,711,774 | 12/1987 | Denick et al. | 424/155 |
| 4,711,784 | 12/1987 | Yang | 426/5 |
| 4,714,620 | 12/1987 | Bunick et al. | 426/572 |
| 4,717,565 | 1/1988 | Denick, Jr. | 424/155 |
| 4,740,376 | 4/1988 | Yang | 426/650 |
| 4,747,881 | 5/1988 | Shaw et al. | 106/209 |
| 4,749,575 | 6/1988 | Rotman | 424/441 |
| 4,752,485 | 6/1988 | Sharma et al. | 426/658 |
| 4,753,800 | 6/1988 | Mozda | 424/440 |
| 4,758,424 | 7/1988 | Denick, Jr. et al. | 424/48 |
| 4,758,425 | 7/1988 | Denick, Jr. et al. | 424/48 |
| 4,761,274 | 8/1988 | Denick, Jr. et al. | 424/48 |
| 4,766,004 | 8/1988 | Moskowitz | 426/658 |
| 4,774,099 | 9/1988 | Feeney et al. | 426/552 |
| 4,778,676 | 10/1988 | Yang et al. | 424/79 |
| 4,784,861 | 11/1988 | Gori | 426/74 |
| 4,790,991 | 12/1988 | Shaw et al. | 424/441 |
| 4,797,288 | 1/1989 | Sharma et al. | 424/79 |

Primary Examiner—Shep K. Rose
Attorney, Agent, or Firm—Daniel A. Scola, Jr.; Charles A. Gaglia, Jr.; Craig M. Bell

[57] ABSTRACT

A chewable delivery system for actives comprising:
(a) an active pre-coated with at least one material selected from the group consisting of lecithin, polyoxyalkylenes having chain lengths of about 4 carbons or less, glycerides having a melting point of 100° C. or less, polyalkyleneglycols having a molecular weight of 3,700 or less, synthetic and natural waxes and mixtures thereof; and
(b) a confectionery matrix comprising a binder system comprising gelatin and a humectant material selected from the group consisting of glycerin and its lower alkyl ($C_{2-7}$) ester derivatives; a sweetener; and about 1% to about 30% by weight water.

14 Claims, No Drawings

CONFECTIONERY DELIVERY SYSTEM FOR EXPECTORANTS

This application is a divisional of U.S. Ser. No. 811,601, filed Dec. 20, 1985, now U.S. Pat. No. 4,778,676.

FIELD OF THE INVENTION

The present invention relates to a novel confectionery delivery system for actives such as fiber and drugs. The confectionery delivery system comprises a chewable matrix and an active material, the combination of which is preferably both fat free and non-sucrose-containing, and therefore low in calories. Active materials such as dietary fiber and/or drugs can be incorporated and effectively masked in the delivery system. The unpleasant taste and mouthfeel of the fiber and/or drug is effectively masked and substantial hydration of the active is delayed until the delivery system passes through the oral cavity. The resultant products are substantially more palatable, and are essentially devoid of graininess, bitterness or fibrous texture. The pleasant taste of the delivery system and products made therefrom encourages patient compliance with a recommended therapy.

BACKGROUND OF THE INVENTION

Prescribed daily dosage amounts for fiber are often very high, requiring the patient to administer the fiber or fiber composition several times per day. While their benefits are well known to the consuming public, the unpleasant fibrous mouthfeel and texture of products containing dietary fiber have resulted in reluctance of patients to comply with prescribed dosages.

Patient compliance with prescribed drug therapies is also a problem particularly when the drug has an unpleasant taste, after-taste or gritty mouthfeel. Drugs such as cholestryamine and potassium chloride are known to taste umpleasant. The prior art has disclosed products to mask the taste of these drugs, but the products themselves often suffer from their own unpleasant tastes.

The trend, therefore, in patient use of the prior art products containing fiber or drugs has been to deviate from the prescribed dosage or frequency of dosage, thereby diminishing the effectiveness of the therapy.

Two patents which disclose palatable drug formulations use coacervation techniques to combine cholestyramine with modified celluloses. U.S. Pat. No. 3,974,272 shows oral palatable formulations containing aqueous media and cholestryamine. A method of treating hypercholesterolemia is claimed. Chewable products containing cellulosic/gum colloids are disclosed.

U.K. Patent No. 1,446,352 concerns palatable compositions useful for the treatment of hypercholesterolemia and biliary cirrhosis. The invention provides a liquid composition containing "coacervate of cholestyramine with a cellulose hydrocolloid" derivative. By the term "coacervate" is meant the coagulation of two hydrophilic substances of opposite charge. Representative hydrocolloids are methyl and ethyl cellulose, sodium carboxymethyl cellulose, hydroxyethyl cellulose and hydroxypropyl cellulose. A water-insoluble dispersing agent, e.g., a substituted carboxymethylstarch, is optional. In making the composition, 1 part by weight of hydrocolloid is combined with 4 to 10 parts of cholestyramine by dry mixing and passing through a No. 80 U.S. standard mesh screen. The resulting powder is then mixed with a liquid to form a coacervate which can be orally administered.

With respect to dietary fiber, numerous attempts to mask the fibrous mouthfeel have been tried. Various baked products, granola-type product, cereals and snack-food products have attempted to incorporate fiber in confectionery systems. These products are generally high in caloric value and relatively low in dietary fiber. The objective of the prior art has been to attempt to conceal the unpleasant taste and texture of the fiber by using various materials such as fats, polyhydric alcohols, sugar solids or starch. While the objective is achieved to some degree, these materials increase the caloric value and dilute the effective dose. High amounts of fiber, e.g., amounts greater than about 5%, typically were dry-tasting with an unpleasant fibrous mouthfeel.

Fiber products which are specifically intended for bowel normalization and related disorders include those which are slurried in water. With respect to the prior art attempts to make a fiber product when is added to water and drunk as a slurry, the fiber tended to clump together, forming slimy, unpalatable masses. These fiber clumps were comprised of hydrated hydrocolloids, e.g., pysillium. High amounts of excipients were necessary to minimize clumps. These excipients or dispersing aids were generally carbohydrate or fat materials such as sugar, dextrose and the like, which are high in caloric value.

Conventionally, fiber is incorporated into edible substances as fine powder. There are several reasons for this. Fine powdered fiber is less apt to form "fish-eye" clumps when hydrated, e.g., clumps having a dry center and wet surface. Furthermore, the purification of fiber often involves steps which reduce the particle size of fiber. Few soluble dietary fibers, with the exception of guar gum, hydrate sufficiently or uniformly unless the particle size is fine. Fine particles are, however, difficult to handle and process and products containing above 10 to 15% dietary fiber have unpalatable and fibrous textures.

It is well known that the functionality and effectiveness of fiber and certain drugs such as ion exchange resins is dependent on the active surface area. Fine particles achieve the desired therapeutic effects more effectively than course particles because the former have a higher surface area to weight ratio, e.g., a higher active surface. For example, in the case of ion exchange resins, e.g., cholestyramine, a greater surface area allows enhanced adsorption of bile acids, increased ion exchange, as well as other surface phenomena. In the case of fiber, increased surface area allows for increased adsorption of, and combination with, liquids, body metabolites and the like. The result is increased bulk and swelling upon adsorption which is therapeutically desirable.

While course substrate particles do not have sufficient effective surface area to be as effective as the finer particles, finer particles also suffer from certain handling, processing, and formulation problems. The finer particles, having a larger total surface area than courser particles, tend to be organoleptically perceived as too dry or dusty, and in the case of certain fibers a pasty taste results. These organoleptic characteristics are undesirable. Additionally, when fine particles are added in therapeutic amounts to a delivery matrix, e.g., a confectionery formulation, the fine particles tend to disrupt the continuous phase characteristics of the final product.

THE INVENTION

The present invention relates to a chewable delivery system for actives such as drugs and fibers. The delivery system comprises:

(a) a water insolubilized active pre-coated with at least one material selected from the group consisting of lecithin, polyoxyalkylenes having a chain length 4 or less carbons, glycerides having a melting range of about 100° C. or less, polyalkylene glycols having a molecular weight of about 3,700 or less, synthetic and natural waxes and mixtures thereof; and (b) a confectionery matrix comprising a binder system comprising gelatin and a humectant material selected from the group consisting of glycerin and its lower alkyl ($C_{2-7}$) ester derivatives; a sweetener; and moisture in the amount of about 1% to about 30% by weight.

It is critical to the success of the invention that effective masking of bitterness and undesirable mouthfeel or texture be accomplished. The active materials therefore undergo a treatment prior to their incorporation in the confectionery matrix. Pre-coating of the active is required using one or more of the recited materials. The term "pre-coating" is meant to refer to a variety of conventional techniques which may be used to adhere to, create a film on, or otherwise coat the active material prior to its incorporation in the confectionery matrix. Coating techniques useful include simple mixing, spray congealing, freeze-drying, fluidized-bed granulation, agglomeration, spray-coating, spray-drying and extrusion, as well as other encapsulation techniques well defined in the art.

The particular coating technique employed will depend to a large degree on the type of active chosen. For example, if the active is a dietary fiber, simple mixing or spray-coating is preferred. If the active is a drug such as cholestyramine, simple mixing or fluidized bed granulation may be preferred.

The active is generally present in the final dosage form in therapeutic amounts commensurate with the type of drug or fiber used. Generally, the active and precoating will make up about 15 to about 30% by weight of the total dosage form.

THE PRE-COATING MATERIALS

These materials must be capable of readily adhering and forming, at least a partial, and preferably a full coating on the active. By doing so, the coating provides a barrier to aid in masking any bitterness and/or undesirable textural properties inherent in the active. The barrier also serves to protect the active, from a stability point of view. The coating must, however, allow for proper release of the active and must not interfere with the function or effectiveness of the active. The ratio of coating to active ranges from about 1:11 to about 99:1 parts by weight.

Among those coating materials recited above, lecithin is preferred because of the numerous functions it provides. For example, the emulsifying character of lecithin aids in wetting of the active surface and facilitating its incorporation into the confectionery matrix, as well as aiding in the miscibility of the active when hydrolyzed in solution or saliva. Pure grades of lecithin are preferred, e.g. one where the solids content is about 95% or higher. The lecithin should be of a fraction which is pourable, rather than powder or solid, at room temperature. The Condensed Chemical Dictionary, 9th edition, Van Nostrand Reinhold, 1977, defines lecithin as mixtures of diglycerides of fatty acids linked to the choline ester of phosphoric acid. Lecithins are typically classified as phosphoglycerides or phosphatides. In the instant coatings, lecithin preferably has a minimum of about 95% by weight of phosphatide present. This purity level is generally designated in commercially available lecithins as "95% acetone insolubles." The phrase "95% acetone insolubles" is intended to mean that upon dissolution of the lecithin in acetone, 95% of the phosphatide portion remains insoluble. Residual impurities such as oil, moisture and soluble non-phosphatides account for the 5% of the material dissolves and extracted.

Those polyoxyalkylenes useful as the coating material for the active include polyoxyethylene, polyoxypropylene, polyoxybutylene, copolymers of these, as well as mixtures thereof.

Glycerides which are useful as the coating material for the active should have a melting point or melting range of 100° C. or less, such that they soften in the mouth. The term "glycerides" used herein refers to commonly identified glycerides which are esters of glycerol and fatty acids in which one or more of the hydroxyl groups of the glycerol have been replaced by acid radicals. The glyceride is useful if a hydrophobic coating on the active is desired.

Polyalkylene glycols useful as coatings for the actives include polyethylene glycol, polypropylene glycol, polybutylene glycol and mixtures thereof, among others. As mentioned above, the molecular weight of the polyalkylene glycol should be about 3,700 or less.

Synthetic and natural waxes useful as coatings for the actives include animal waxes, vegetable waxes, petroleum waxes and the like. Specific examples of waxes are beeswax, lanolin, bayberry, candelilla, carnauba, paraffin, microcrystalline petrolatum and carbowax. Mixtures of these waxes are also useful.

The pre-coating materials may be used in amounts of about 1 to about 10% by weight of the total delivery system and preferably in amounts of about 2 to about 6%.

THE ACTIVES

The term "active" means the fiber or drug materials referred to herein which are incorporated into the confectionery delivery matrix either in the pre-coated or uncoated form.

The term "edible" is meant to include all materials which are used by, or which perform a function in, the body. Thus, materials which are not adsorbed or absorbed are included as well as non-digestible and digestible materials.

The term "fine" particles indicates a standard U.S. U.S. mesh size number of greater than about 70. The term "coarse" particles indicates a standard U.S. mesh size number of less than about 70.

The term "dietary fiber" is understood to mean the component of food which is non-digestible and non-metabolizible by humans. It is well known, however, that dietary fibers as they occur naturally in food sources also have associated with them a small digestible portion comprising fats, proteins, and carbohydrates.

Dietary fiber can be divided into two broad categories: insoluble dietary fiber and water soluble dietary fiber. For purposes of this invention, "insoluble dietary fiber" means the water insoluble portion of an edible material remaining after chemical and enzymatic treatment has removed proteins, fats and carbohydrates. For example, brans, celluloses, hemicelluloses lignin and the like, are among those useful. "Soluble dietary fiber" means dietary fiber which is the water soluble portion of an edible material remaining after the chemical and enzymatic treatment has removed proteins, fats and carbohydrates. For example, pectin, guar gum, locust bean gum, gum arabic, karaya gum and others from the galacturonan and glactomannan classes; as well as psyllium seed gum, carageenan, konjac mannan, among others. These soluble fibers have been known to inhibit absorption of cholesterol in mammals, as well as re-absorption of bile salts. The mechanism for this benefit is believed to be three-fold in nature. First, the shear mass of the swelled fiber occludes the cholesterol and bile salts, thereby preventing absorption. Second, the fibers will absorb the cholesterol and bile salts, thereby physically transporting out of the body. Finally, the fibers increase the transit time of stool bulk, which decreases the time in which absorption of cholesterol and bile salts can occur. Dietary fiber provides the bulking effect commonly associated with fiberous materials.

Useful dietary fiber substances include noncellulosic polysaccharides, pectin, gums, algal polysaccharides, cellulose, hemicellulose, lignin, mucilages and mixtures thereof. The dietary fiber is present in the delivery system in amounts of about 1% to about 75% by weight; preferably in amounts of about 10 to about 30%; and most preferably about 12 to about 25%.

The term "drug" when used to classify the active includes medicaments, vitamins, mineral supplements and other chemical or biological substances intended for use in the treatment, prevention, diagnosis, cure or mitigation of disease or illness, or substances which affect the structure or function of the body. Mixtures are operable.

Suitable categories of drugs that may be employed in the instant aggregate may vary widely and generally represent any stable drug combination. Illustrative categories and specific examples include:

(a) Antitussives, such as dextromethorphan, dextromethorphan hydrobromide, noscapine, carbetapentane citrate, and chlophedianol hydrochloride;

(b) Antihistamines, such as chlorpheniramine maleate, phenindamine tartrate, pyrilamione maleate, doxylamine succinate, and phenyltoloxamine citrate;

(c) Decongestants, such as phenylephrine hydrochloride, phenylpropanolamine hydrochloride, pseudoephedrine, hydrochloride ephedrine;

(d) Various alkaloids, such as codeine phosphate, codeine sulfate and morphine;

(e) Mineral supplements such as potassium chloride and calcium carbonates, magnesium oxide and other alkali metal and alkaline earth metal salts;

(f) Laxatives, vitamins and antacids;

(g) Ion exchange resins such as cholestyramine;

(h) Anti-cholesterolemic and anti-lipid agents such as gemfibrozil;

(i) Antiarrhythmics such as N-acetyl-procainamide;

(j) Antipyretics such as acetominophen, aspirin and ibuprofen;

(k) Appetite suppressants such as phenylpropanolamine hydrochloride or caffeine; and (l) Expectorants such as guaifenesin.

Additional useful active medicaments include anti-inflammatory substances, coronary dilators, cerebral dilators, peripheral vasodilators, anti-infectives psychotropics, antimanics, stimulants, gastro-intestinal sedatives, antidiarrheal preparations, anti-anginal drugs, vasodilators, anti-hypertensive drugs, vasoconstrictors and migrane treatments, antibiotics, tranquilizers, antiphychotics, antitumor drugs, anticoagulants and antithrombotic drugs, hypnotics, sedatives, antiemetics, anti-nauseants, anticonvulsants, neuromuscular drugs, hyper- and hypoglycaemic agents, thyroid and antithyroid preparations, diuretics, antispasmodics, uterine relaxants, nutritional additives, antiobesity drugs, anabolic drugs, erythropoietic drugs, antiasthmatics, cough suppressants, mucolytics, anti-uricemic drugs, and the like.

Mixtures of the drugs and medicaments may also be used.

The preferred drugs are cholestyramine and potassium chloride. Cholestyramine is the chloride salt of a basic anion exchange resin which has an affinity for sodium chloride and a particularly strong affinity for acid materials such as bile acids. It occurs as a white powder, insoluble in water and has an amine-like odor and a gritty taste. Cholestyramine is believed to absorb and combine with bile acids in the intestine to form an insoluble complex which is then excreted by the body. Cholesterol is the major precusor of bile acids which are formed by the oxidation of cholesterol. The serum level of cholesterol can be reduced by administration of cholestyramine, which leads to reduction of bile acids and increased oxidation of cholesterol.

The recommended adult dosage of cholestyramine is about 5 to about 50 grams per day; preferably about 12 to about 32 grams per day. Administration is generally about 3 or 4 times daily in dosages of about 2 to 10 and preferably about 3 to 4 grams.

Potassium chloride is generally sold as a powder or tablet to be dissolved in cold water. Adult dosages are generally about 1.02 to about 2.56 grams (40–100 MEq) per day, administered in amounts of about 50 MEq about 1 or 2 times per day.

The drug is present in the delivery system in amounts of about 0.1 to about 85% by weight; preferably about 5 to about 50%; and most preferably about 10 to about 30%.

THE CONFECTIONERY MATRIX

While the texture, physical attributes and form of the delivery system can be varied widely by alternating the ratio of ingredients within the given ranges, it is preferred that the delivery system be chewy in consistency and texture. This "chewiness" is preferably smooth and creamy in nature, although the courseness or smoothness may be balanced as desired.

This chewy delivery system is novel in that it is very different in texture and physical form from the prior art gels and nougats. This is primarily due to the unique combination of ingredients and balance of the moisture content, which must be maintained within the range of about 1 to about 30% by weight. Outside these ranges, the delivery system fails to be operable. Too low a moisture content results in a brittle and crumbly product which is neither palatable or effective in masking actives. At higher limits of moisture, microorganism growth becomes a problem and the texture loses its chewiness. Water must by physically trapped in the structure of the delivery system in order to maintain the structural integrity of the final product.

The binder system comprises gelatin and a humectant material which when combined with the water provides structure to the delivery system. The sweetener adds to the bulk as well as the sweetness of the delivery system.

The sweetener is generally selected from a wide variety of materials and is present in amounts of about 6 to about 70%, preferably about 30 to about 50% and most preferably about 40 to about 45% by weight of the composition. Representative, but non-limiting examples of sweeteners include xylose, ribose, glucose, mannose, galactose, fructose, dextrose, maltose, partially hydrolyzed starch, lactose, hydrogenated starch hydrolysate and mixtures thereof. In addition to these sweeteners, polyhydric alcohols such as sorbitol, mannitol, xylitol, and the like may also be incorporated as well as a variety of artificial sweeteners. Among those artificial sweeteners useful include amino acid based sweeteners, dipeptide sweeteners, saccharin and salts thereof, acesulfame salts, cyclamates, steviosides, dihydrochalcone compounds, talin, glycyrrhizin and mixtures thereof.

The binder system contains gelatin in amounts of about 0.1 to about 5% and preferably about 0.5 to about 3.0% by weight of the final delivery system. A 250 bloom grade of gelatin is preferred, although not critical to the practice of this invention. By the term "gelatin" is meant a heterogenous mixture of water-soluble proteins of high average molecular weight derived from collagen by hydrolytic action. The gelatin structure is modified by the incorporation of glycerin and its lower alkyl ester derivatives. Glycerin provides a water binding capacity to aid in the maintenance of the water balance. Glycerin is incorporated in amounts of about 0.1 to about 25% and preferably about 2% to about 9% by weight of the final delivery system. The combination of gelatin and the glycerin or glycerin derivatives provides a chewiness as well as structure to the final product. This combination is critical to the invention. Gelatin without glycerin or its derivatives would yield a composition and final product which would have sufficient structural integrity as a product, but would lack the smooth, chewy texture necessary to obtain the proper mouthfeel for masking the active materials. Without glycerin or its derivatives the product would be too tough to chew and would not be as palatable or attractive to the consumer. It is preferred that a thermoreversible gelatin be used to aid in obtaining homogeniety as well as to provide processing convenience.

The delivery system in its final form can be classified as a semi-solid, intermediate moisture system, having some properties clearly identified with those of gels and some properties that are similar to the nougat variety of confectioneries. The inventive delivery systems are quite distinguishable over conventional gels and nougats in texture, structure and chew properties.

Flavors which may optionally be added to the delivery system are those well known in the confectionery art. For example, synthetic flavor oils, and/or oils derived from plants, leaves, flowers, fruits and so forth, and combinations thereof are useful.

Representative flavor oils include spearmint oil, peppermint oil, cinnamon oil, and oil of wintergreen (methylsalicylate). Also useful are artificial, natural or synthetic fruit flavors such as citrus oils including lemon, orange, grape, lime and grapefruit, and fruit essences including apple, strawberry, cherry, pineapple and so forth.

The amount of flavoring agent employed is normally a matter of preference subject to such factors as flavor type, base type and strength desired. In general, amounts of about 0.01% to about 5.0% by weight of the final product are useful with amount of about 0.02% to about 1.5% being preferred and about 0.03% to about 1.2% being most preferred.

In a preferred embodiment, the inventive delivery system is substantially fat-free and sucrose-free. This type of formulation is designed for those, who for dietetic reasons, are required to regulate their intake of fats and sugar. A typical preferred embodiment is as follows:

| Ingredient | % by weight | Preferred range % by weight |
| --- | --- | --- |
| Lecithin | 4.00 | 2.0–6.0 |
| Cholestyramine resin | 20.00 | 10.0–30.0 |
| Fructose | 43.84 | 40.0–45.0 |
| Sorbitol | 12.00 | 8.0–45.0 |
| Gelatin | 1.00 | 0.5–3.0 |
| Glycerin* | 5.00 | 2.0–9.0 |
| Hydrocolloid** | 0.10 | |
| Pectin | 1.50 | 0–10 |
| Citric acid | 0.50 | 0.3–1.50 |
| Flavor/color | 0.06 | 0.03–1.2 |
| Water | 12.00 | 8.0–15.0 |

*Anhydrous 99.5%
**Represents 0.04% guar gum and 0.04% locust bean gum

This embodiment has been found to be particularly good for masking the grittiness of the cholestyramine and is as effective as the prior art cholestyramine systems at delivering a clinically effect dosage of the drug to the patient.

If the active is cholestyramine resin, an equilibrium must be maintained with respect to the water content of the delivery system. The equilibrium relative humidity (ERH) of the confectionery matrix and the pre-coated cholestyramine must be approximately the same such that little water exchange between the resin and the matrix occurs. Additionally, the matrix must be capable of preventing loss of moisture into the atmosphere. Losing water from the matrix will cause the matrix to lose its unique chewy character and become brittle. Migration of water from the resin to the vehicle will cause the resin structure to collapse, thereby destroying the resin channels necessary for bile absorption.

The inventive delivery systems are prepared without excessive heat, e.g., lower than the boiling point of water, to maintain bound moisture in the cholestyramine resin.

OPTIONAL MATERIALS

The edible matrix of this invention may likewise contain additional conventional additives, including fillers and mineral adjuvants such as calcium carbonate, magnesium carbonate and talc; emulsifiers; coloring agents such as titanium dioxide; fats and oils such as partially hydrogenated palm kernel oil and coconut oil; starches such as modified corn starch and tapioca dextrin as well as other conventional confectionery additives well known in the confectionery art.

In one embodiment compound coating, chocolate ingredients and the like have been effectively employed in coating the delivery system. For example, the delivery system can be formed into a candy bar shape and enrobed with chocolate or caramel.

Hydrocolloid materials are optional but useful in the instant invention as a texture modifier. The hydrocolloid is mixed into the delivery system in a hydrated or powder form. If the hydrocolloid is a dietary fiber it is preferably added in powdered form. Upon hydration, e.g., in saliva, the hydrocolloid becomes slippery almost immediately. This slippery characteristic imparts lubricity to the particles to aid in masking the active. The hydrocolloid thus modifies the physical characteristics of the delivery system matrix. The hydrocolloid functions to bind fine particles of the active together and at higher concentrations increases lubricity in the mouth. The lubricity is primarily due to the slippery nature of the hydrated hydrocolloid surface. This characteristic is an advantage in that the mouthfeel perception of the consumer is such that the particles are smooth and easy to swallow, being devoid of unpleasant texture or taste.

The hydrocolloid material must, however, be one which does not interfere with the functionality of the active. For example, if an anion-exchange resin such as cholestyramine is used as the active, nonionic hydrocolloid materials such as guar gum or locust bean gum should be used. This is in contrast to the prior art cholestryamine patents, e.g., U.S. Pat. No. 3,974,272, where anionics are added. If cholestyramine is used as the active in the inventive delivery systems, anionic hydrocolloid materials are not useful since they would tend to bind with the resin, leaving them less binding capacity to bind with bile resins. Other hyrocolloid materials are contemplated, however, with a variety of other actives. Among those hydrocolloid materials useful include natural and modified gums, e.g., locust bean gum, guar gum, carageenan, among others; celluloses and modified celluloses, pectin, mucilages, modified starch, non-cellulosic polysaccharides, algal polysaccharides and mixtures thereof.

Hydrocolloid materials are optionally present in amounts of about 0% to about 0.1% and preferably in amounts of about 0.02 to about 0.06% by weight.

PROCESS OF PREPARATION

In general, the delivery system can be prepared by pre-coating the active, and adding it to the confectionery matrix in a simple mixing procedure. Pre-coating can be accomplished using any of the aforementioned coating techniques. With respect to preparation of the confectionery matrix, gelatin and glycerin are first mixed together in water along with any optional hydrocolloid materials, until uniformity is obtained. The sweetener(s) is/are then added, while mixing is continued, and the pre-coated active is then mixed in as well. Additional glycerin may be added at this point, along with flavor, color, pectin and other conventional ingredients. The final mixture is then formed into the desired dosage piece size and wrapped for distribution.

In the preparation of a typical preferred embodiment, e.g., the non-fat, non-sucrose cholestyramine resin example described herein, the cholestyramine is first separately coated with lecithin using a simple mixing technique. For example, the purified grade of lecithin is added at ambient temperature, along with the cholestyramine resin to a Hobart mixer set at a medium mixing speed. The lecithin must be a liquid material at room temperature such that it will flow around and coat the solid resin particles. Adequate coating of the resin is obtained in about 20 to 30 minutes.

In a separate container, preparation of the confectionery matrix is begun by preparing an aqueous solution of guar gum and locust bean gum. A gelatin/-glycerin aqueous solution is then added to the guar gum/locust bean gum solution and mixed until uniform. Fructose and sorbitol are then dissolved in this solution and the pre-coated active is added at this point. Additional glycerin, flavor, pectin, color and other conventional confectionery additives may be added at this stage and mixing is continued until uniformity is obtained. The mixture is then extruded using a Hutt twin screw extruder to form a bar-shaped configuration having a 20 gram weight. The product is then ready for packaging.

The following examples serve to provide further appreciation of the invention but are not meant in any way to restrict the effective scope of the invention. All percentages throughout the specification and claims are by weight of the final delivery system unless otherwise indicated.

EXAMPLE I

Delivery systems were prepared in the manner discussed above, using the following formulation:

| Ingredient | Delivery system - % Weight | | | | |
| --- | --- | --- | --- | --- | --- |
|  | A | B | C | D | E |
| Cholestyramine resin | 20 | 25 | 30 | 35 | 40 |
| Lecithin | 2.5 | 2.5 | 3.0 | 3.0 | 3.6 |
| Fructose | 40 | 40 | 38 | 35 | 30 |
| Sorbitol | 7 | 5 | — | — | — |
| Mannitol | 5 | 2 | — | — | — |
| Guar gum | 0.04 | 0.04 | 0.07 | 0.1 | 0.1 |
| Locust bean gum | 0.04 | 0 04 | 0.07 | 0.1 | 0.1 |
| Water | 16 | 16 | 18 | 16 | 16 |
| Gelatin | 2.5 | 2.5 | 3.0 | 3 | 3 |
| Glycerin | 5.22 | 5.22 | 6.16 | 6.1 | 6.0 |
| Flavor | 1.7 | 1.7 | 1.7 | 1.7 | 1.2 |
|  | 100 | 100 | 100 | 100 | 100 |

These formulations represent delivery systems which are non-fat, non-sucrose containing. The resultant mixtures were extruded into various shapes, e.g., bars and chunks, and tested for organoleptic and clinical efficacy. The results showed that each of the delivery system formulations were effective in masking the taste of the drug and providing a smooth texture devoid of graininess. Clinical tests showed effective release and availability of the drug both in vitro and in vivo.

EXAMPLE II

Delivery systems F and G were prepared having a laxative dosage of dietary fiber as the active. The formulations were respectively identical to formulation A and C of Example I, except that oat bran was substituted for the cholestyramine.

EXAMPLE III

Delivery systems were prepared according to the formulations below using gemfibrozil and potassium chloride as actives.

| Ingredient | Delivery system* - % weight | |
| --- | --- | --- |
|  | H | I |
| Gemfibrozil | 1.5 (300 mg) | — |
| Potassium chloride | — | 6.4 (1.28 g) |
| Lecithin | 2.5 | 3.0 |
| Fructose | 58.8 | 61.6 |
| Sorbitol | 7 | — |

-continued

| Ingredient | Delivery system* - % weight | |
|---|---|---|
| | H | I |
| Mannitol | 5 | — |
| Water | 16 | 18 |
| Gelatin | 2.5 | 3 |
| Glycerin | 5 | 6.3 |
| Flavor | 1.7 | 1.7 |
| | 100 | 100 |

*Based on a 20 gram dosage piece.

EXAMPLE IV

The delivery systems of this example demonstrate the use of sweetners other than fructose.

| Ingredient | Delivery system* - % weight | |
|---|---|---|
| | J | K |
| Cholestryamine resin | 20.0 | 30 |
| Lecithin | 2.5 | 3.0 |
| Lycasin | 52.00 | — |
| Polydextrose | — | 37.5 |
| Sodium saccharin | — | 0.5 |
| Guar gum | 0.04 | 0.07 |
| Locust bean gum | 0.04 | 0.07 |
| Water | 16.0 | 18.0 |
| Gelatin | 2.5 | 3.0 |
| Glycerin | 5.22 | 6.16 |
| Flavor | 1.7 | 1.7 |
| | 100 | 100 |

EXAMPLE V

This example demonstrates the use of a combination of dietary fiber (pectin) and cholestyramine as actives in the delivery system.

| Ingredient | Delivery system* - % weight | |
|---|---|---|
| | L | M |
| Cholestryamine resin | 15.0 | 20.0 |
| Pectin | 5.0 | 10.0 |
| Lecithin | 2.5 | 3.5 |
| Fructose | 40.0 | 38.0 |
| Sorbitol | 7.0 | — |
| Mannitol | 5.0 | .0 |
| Water | 16.0 | 18.0 |
| Gelatin | 2.5 | 3.0 |
| Glycerin | 5.3 | 6.16 |
| Flavor | 1.7 | 1.7 |

The invention being thus described, it will be obvious that the same may be varied in many way. Such variations are not to be regarded as a departure from the spirit and scope of the invention and all such modifications are intended to be included within the scope of the following claims.

We claim:

1. A chewable confectionery delivery system for expectorants comprising:
   (a) an expectorant pre-coated with at least one material selected from the group consisting of lecithin, polyoxyalkylenes having chain lengths of about 4 carbons or less, glycerides having a melting point of 100° C. or less, polyalkyleneglycols having a molecular weight of 3,700 or less, synthetic and natural waxes and mixtures thereof; and
   (b) a confectionery matrix comprising a binder system comprising from about 0.1% to about 5% by weight gelatin and a humectant material selected from the group consisting of glycerin and its lower alkyl ($C_{2-7}$) ester derivatives, a sweetener; and about 1% to about 30% by weight water, all weights are in percent of the final delivery system.

2. The delivery system of claim 1 wherein the material used for the pre-coating of the active is present in amounts of about 1 to about 10% by weight of the total delivery system.

3. The delivery system of claim 1 wherein the ratio of coating to achive is about 1:3 to about 1:8 parts by weight.

4. The delivery system of claim 1 wherein the material used for the pre-coating of the active is selected from the group consisting of polyoxyethylene, polyoxypropylene, polyoxybutylene, copolymers of these and mixtures thereof.

5. The delivery system of claim 1 wherein the polyalkyleneglycol is selected from the group consisting of polyethyleneglycol, polypropyleneglycol, polybutyleneglycol and mixtures thereof.

6. The delivery system of claim 1 wherein the binder system comprises about 0.1 to about 5.0% gelatin and about 0.1 to about 25% of the humectant material.

7. The delivery system of claim 6 wherein the humectant is selected from the group consisting of glycerine, triacetin, tributyrin and mixtures thereof.

8. The delivery system of claim 1 wherein there is additionally incorporated a nonionic hydrocolloid gum.

9. The delivery system of claim 8 wherein the gum is selected from the group consisting of guar gum, locust bean gum, and mixtures thereof.

10. The delivery system of claim 1 wherein there is additionally included a material selected from the group consisting of pectin, sweeteners, flavorings, colorings, humectants, fillers, emulsifiers, thickeners, and mixtures thereof.

11. The delivery system of claim 1 wherein the pre-coated expectorant is present in a pharmaceutically effective amount.

12. The delivery system of claim 1 wherein the pre-coated expectorant comprises about 15 to about 30% by weight of the final product.

13. The delivery system of claim 1 wherein the expectorant is guaifenesin.

14. A method of preparing a confectionery delivery system for expectorants comprising:
   (a) pre-coating the expectorants with at least one material selected from the group consisting of lecithin, polyoxyalkylenes having a chain length of about 4 carbons or less, glycerides having a melting point of 100° C. or less, polyalkyleneglycols having a molecular weight of 3,700 or less, synthetic and natural waxes and mixtures thereof, wherein the coating does not interfere with the function or release of the active; and
   (b) preparing a confectionery matrix comprising the steps of (i) forming a solution of gelatin and a humectant selected from the group consisting of glycerin and its lower alkyl ($C_{2-7}$) ester derivatives; a sweetener; and about 1% to about 30% by weight water; and
   (c) admixing mixtures from (a) and (b) together; and
   (d) forming the resultant delivery system into shapes.

* * * * *